United States Patent
Anderson et al.

(10) Patent No.: US 10,183,104 B2
(45) Date of Patent: **\*Jan. 22, 2019**

(54) MODULAR IMPLANTABLE VENTRICULAR ASSIST DEVICE

(71) Applicant: Medtronic Vascular Galway, Ballybrit, Galway (IE)

(72) Inventors: Marc Anderson, Ballybrit (IE); Declan Costello, Ballybrit (IE); Marian Creaven, Ballybrit (IE); Paul Devereux, Ballybrit (IE); Niall Duffy, Ballybrit (IE); John Gallagher, Ballybrit (IE); John Milroy, Ballybrit (IE)

(73) Assignee: Medtronic Vascular Galway, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/448,856

(22) Filed: Mar. 3, 2017

(65) Prior Publication Data

US 2017/0173242 A1 Jun. 22, 2017

Related U.S. Application Data

(63) Continuation of application No. 14/636,259, filed on Mar. 3, 2015, now Pat. No. 9,616,159.
(Continued)

(51) Int. Cl.
*A61B 18/00* (2006.01)
*A61M 1/12* (2006.01)
(Continued)

(52) U.S. Cl.
CPC .............. *A61M 1/122* (2014.02); *A61F 2/82* (2013.01); *A61M 1/1025* (2014.02);
(Continued)

(58) Field of Classification Search
USPC .......................................................... 600/16
See application file for complete search history.

(56) References Cited

U.S. PATENT DOCUMENTS 6,136,025 A 10/2000 Barbut et al.
7,144,364 B2 12/2006 Barbut et al.
(Continued)

FOREIGN PATENT DOCUMENTS

CN 102573703 A 11/2012
WO WO 2009/046096 A1 4/2009
(Continued)

OTHER PUBLICATIONS

Alba, et al. "The Future is Here: Ventricular Assist Devices for the Failing Heart" Expert Rev Cardiovasc Ther. 2009; 7(9): 1067-1077.
(Continued)

*Primary Examiner* — Nicole F Johnson

(57) ABSTRACT

The invention features modular implantable ventricular assist devices configured to be, at least in part, assembled within a patient. The devices generally include a pump assembly and an expandable frame. The frame is configured to engage tissue of a patient when implanted. The pump assembly is configured to be operably coupled to the frame when the frame is implanted and in the expanded configuration.

16 Claims, 10 Drawing Sheets

Related U.S. Application Data

(60) Provisional application No. 61/948,236, filed on Mar. 5, 2014.

(51) Int. Cl.
  *A61M 1/10* (2006.01)
  *A61F 2/82* (2013.01)

(52) U.S. Cl.
  CPC ............ *A61M 1/125* (2014.02); *A61M 1/101* (2013.01); *A61M 1/1008* (2014.02); *A61M 1/1098* (2014.02); *A61M 2210/125* (2013.01)

(56) References Cited

U.S. PATENT DOCUMENTS

| | | |
|---|---|---|
| 7,841,976 B2 | 11/2010 | McBride et al. |
| 7,942,804 B2 | 5/2011 | Khaw |
| 8,449,443 B2 | 5/2013 | Rodefeld et al. |
| 2010/0249489 A1 | 9/2010 | Jarvik |
| 2011/0004046 A1 | 1/2011 | Campbell et al. |
| 2011/0071338 A1 | 3/2011 | McBride et al. |
| 2011/0098805 A1 | 4/2011 | Dwork et al. |
| 2011/0257462 A1 | 10/2011 | Rodefeld et al. |
| 2012/0172654 A1* | 7/2012 | Bates ................ A61F 2/01 600/16 |
| 2012/0172655 A1 | 7/2012 | Campbell et al. |
| 2012/0172656 A1 | 7/2012 | Walters et al. |
| 2012/0178986 A1 | 7/2012 | Campbell et al. |
| 2013/0066140 A1 | 3/2013 | McBride et al. |

FOREIGN PATENT DOCUMENTS

| | | |
|---|---|---|
| WO | WO 2009/091965 A1 | 7/2009 |
| WO | WO 2013/148697 A1 | 10/2013 |

OTHER PUBLICATIONS

Office Action for Chinese Patent Application No. 201580011894.7, dated Apr. 3, 2018, 13 pages.

\* cited by examiner

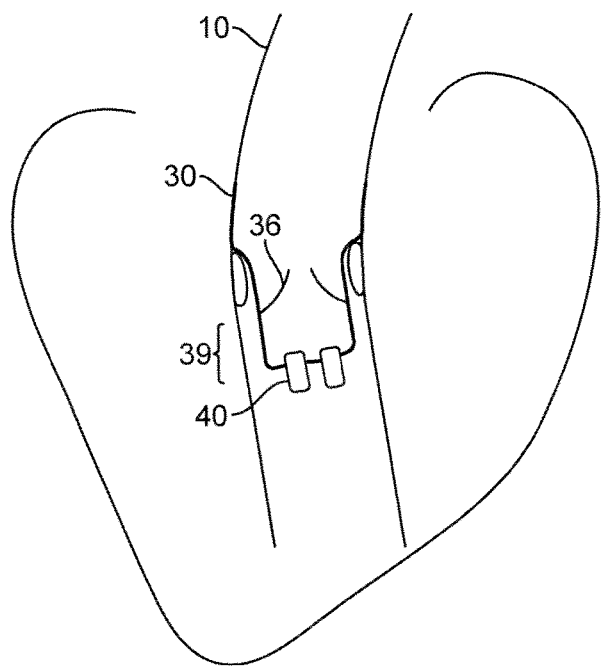
FIG. 3A
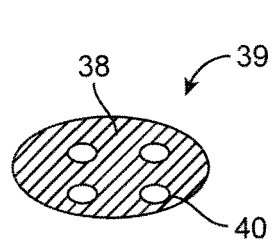 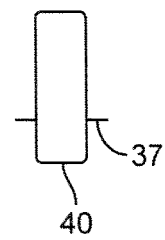
FIG. 3B   FIG. 3C

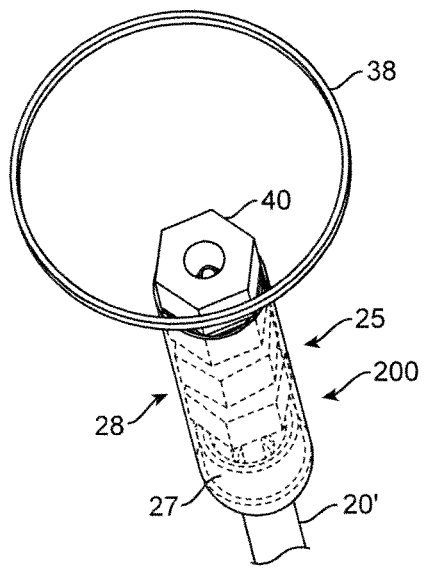
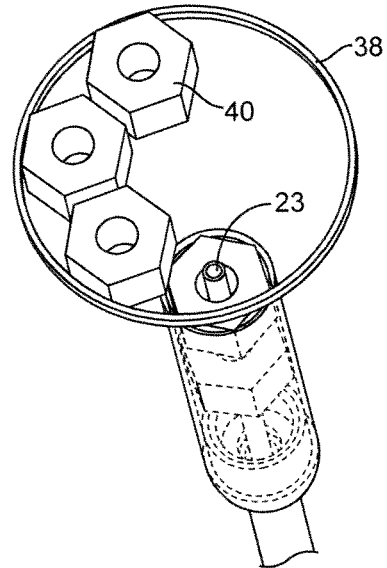
FIG. 6A  FIG. 6B
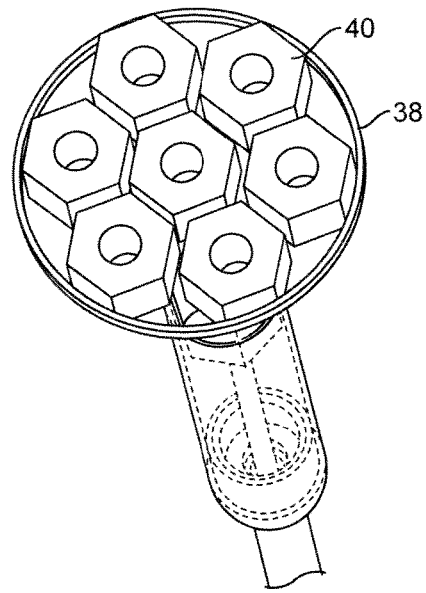
FIG. 6C

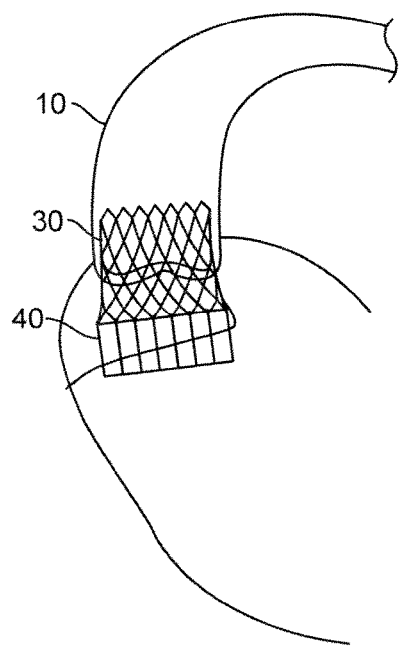
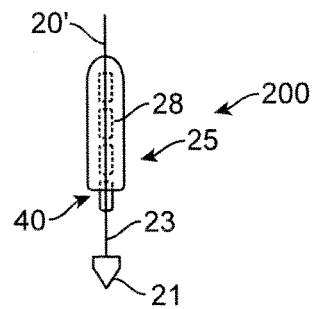
FIG. 9A    FIG. 9B
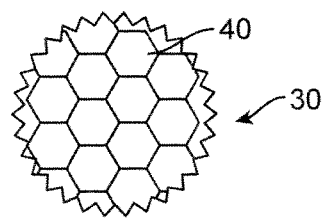
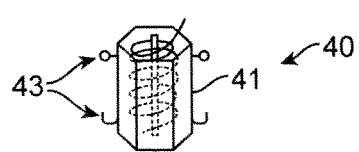
FIG. 9C    FIG. 9D

MODULAR IMPLANTABLE VENTRICULAR ASSIST DEVICE

RELATED APPLICATIONS

This application is a Continuation of and claims the benefit of U.S. patent application Ser. No. 14/636,259 filed Mar. 3, 2015, now U.S. Pat. No. 9,616,159, which claims priority to U.S. Provisional Application No. 61/948,236, filed Mar. 5, 2014. The disclosures of which are herein incorporated by reference in their entirety.

FIELD

This disclosure generally relates to, among other things, implantable ventricular assist devices; particularly to modular implantable ventricular assist devices that can be, at least in part, assembled within a patient.

BACKGROUND

Ventricular assist devices (VADs) are mechanical pumps that take over the function of a damaged ventricle in a heart failure (HF) or other appropriate patient in order to reestablish normal hemodynamics and end-organ blood flow. In addition, VADs unload the native heart allowing it to rest and, in some cases, the heart can recover function. They can be used as short-term support (days) or as long-term support (weeks or months). VADs can support the right, left or both ventricles. In a left VAD (LVAD) an inflow cannula is connected to the apex of the left ventricle and an outflow cannula is connected to the ascending aorta, whereas in a right VAD (RVAD), the inflow cannula is connected to either right atrium or ventricle and the outflow cannula is connected to the pulmonary artery. The pump can be placed outside the patient's body (extra- or para-corporeal devices) or within the abdomen in a preperitoneal position immediately under the diaphragm or above the diaphragm in the pericardial space (intracorporeal devices).

First generation VADs include pulsatile volume displacement pumps and two valves (outflow and inflow valves). The pumps are driven by either pneumatic or electrical drive systems. Examples of these devices are the commercially available THORATEC PVAD, IVAD, and HEARTMATE XVE, and the no longer commercially available THORATEC HEARTMATE IP1000 and VE, the WORLDHEART NOVACOR and the Arrow International LIONHEART LVD2000.

Second generation VADs include implantable, continuous flow, rotary pumps with axial flow that offer several advantages over the first-generation devices. Some of the advantages are the smaller size that reduces the risk of infections and simpler implantation. There are fewer moving parts, absence of valves to direct blood flow, smaller blood-contacting surfaces and reduced energy requirements that enhance simplicity and durability. These pumps have an internal rotor within the blood flow path that is suspended by contact bearings, which imparts tangential velocity and kinetic energy to the blood. The net action results in generation of a net pressure rise across the pump. An external system driver connected by a percutaneous lead powers the pump. Some of the greatest limitations of this type of device are hemolysis, ventricular suction, thrombus formation and pump stoppage. Examples of these devices are the commercially available THORATEC HEARTMATE II, the JARVIK HEART JARVIK 2000 and the MICROMED HEART ASSIST 5.

Third-generation VADs include centrifugal continuous-flow pumps with an impeller or rotor suspended in the blood flow path using a noncontact bearing design, which uses either magnetic or hydrodynamic levitation. The levitation systems suspend the moving impeller within the blood field without any mechanical contact, thus eliminating frictional wear and reducing heat generation. This feature promises longer durability and higher reliability with low incidence of device failure and need for replacement. Usually, magnetic levitation devices are larger owing to the need for complex position sensing and control system that increases requirements for a large pump size. Examples of these devices are the commercially available TERUMO DURAHEART and the HEARTWARE HVAD, the in development Sun Medical Technology EVAHEART LVAS and the no longer commercially available VENTRACOR VENTRASSIST.

All of the VADs discussed above include a pump external to the patient's vasculature and tubing from the pump to a chamber of the patient's heart, aorta or pulmonary artery. In any case, implantation procedures for such VADs are typically invasive.

SUMMARY

This disclosure describes, among other things, VADs that are implantable in a minimally invasive manner and methods for implanting such VADs. In embodiments, the VADs are contained entirely within a patient's cardiovascular system. In embodiments, the VADs are implanted transvascularly, which can be similar to a manner of transcatheter aortic valve implantation.

In embodiments described herein, a ventricular assist device includes a frame having an expanded configuration and a collapsed configuration. The frame, in the expanded configuration, is configured to engage tissue of a patient, such as an inner wall of a blood vessel, when implanted. The ventricular assist device further includes a pump assembly having one or more components configured to operably couple to the frame when the frame is implanted and in the expanded configuration.

In embodiments described herein, a method includes implanting a frame in a vessel of a patient. The frame has a structural scaffold configured to engage the vessel and a lumen defined therethrough. The method further includes operably coupling one or more components of a pump assembly to the frame after the frame is implanted in the vessel.

In embodiments described herein, a method includes deploying a frame in a vessel of a patient. The frame engages the vessel when deployed. The method further includes operably coupling one or more components of a pump assembly to the deployed frame, such that the pump assembly is configured to pump fluid through the frame along a longitudinal axis of the frame.

One or more embodiments of the apparatuses, systems or methods described herein provide one or more advantages over prior ventricular assist devices. For example the ventricular assist devices described in embodiments herein can be implanted in a minimally invasive manner via a transcatheter. The ventricular assist devices, in embodiments, are modular to allow several smaller, lower profile components to be assembled within the patient. By making the ventricular assist devices modular and having lower profile components, the components may be delivered via a transcatheter where fully assembled assemblies having larger profiles may not be amenable to transcatheter implantation.

These and other advantages will be readily understood by those of skill in the art from the following detailed description.

BRIEF DESCRIPTION OF THE DRAWINGS

FIGS. 3A-C are schematic diagrams of embodiments of a ventricular assist device or components thereof.

FIGS. 6A-C are schematic diagrams of embodiments of a ventricular assist device, a delivery system, or components thereof.

FIGS. 9A-D are schematic diagrams of embodiments of a ventricular assist device, a delivery system, or components thereof.

Figure 1A:
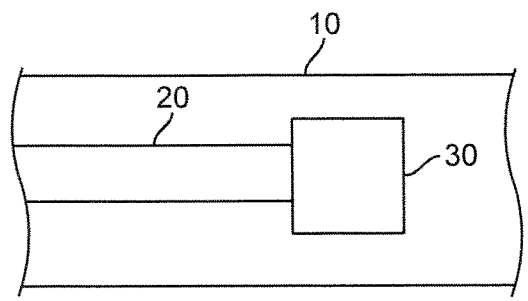
FIGS. 1A-D are schematic sectional diagrams showing stages of an embodiment of implanting a frame within an vessel of a patient and coupling pumps or pump components to the frame.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

This disclosure generally relates to, among other things, VADs that are implantable in a minimally invasive manner and methods for implanting such VADs. In embodiments, the VADs are contained entirely within a patient's cardiovascular system. In embodiments, the VADs are implanted transvascularly, which can be similar to a manner of transcatheter aortic valve implantation.

In embodiments described herein, a ventricular assist pump device assembly includes a frame having an expanded configuration and a collapsed configuration having generally smaller diametric dimensions than the expanded configuration. In the expanded configuration, the frame is configured to engage tissue of a patient such that the frame is anchored relative to the tissue of the patient. The device assembly further includes a pump assembly having one or more components configured to operably couple to the frame when the frame is implanted and in the expanded configuration. Thus final assembly of the device assembly can occur within a patient.

In embodiments, the one or more components of the pump assembly are advanced through the patients vasculature to the frame or one or more components of the pump assembly a distance of greater than 50 cm, such as 100 cm or more, or 200 cm or more.

In embodiments, the frame, in a collapsed configuration, is delivered to a desired location of the patient via a catheter. Once properly positioned, the frame is expanded or allowed to expand to engage tissue of the patient. In embodiments, the one or more pump components are delivered via a catheter and are operably coupled to the expanded frame that is implanted in the patient.

In embodiments, the frame is configured to engage an inner wall of a vessel of the patient, such as a vein or an artery. In embodiments, the frame is configured to engage the aorta of a patient when the frame is in the expanded configuration.

The frame of a ventricular assist pump device assembly can be a frame of a replacement heart valve, such as a frame of a Medtronic COREVALVE replacement heart valve, or substantially similar to a frame of a replacement heart valve. In embodiments, an entire replacement heart valve (as opposed to just the frame) may be employed.

In embodiments, the frames include a series of wires or wire segments. In embodiments, the frames are formed from a single piece of material. For example, the frames may be laser-cut from a single piece of material.

The frames are configured such that they are capable of transitioning from a collapsed configuration to an expanded configuration. In the collapsed configuration, the frame has a smaller diametric dimension than in the expanded configuration. The frame may be compressed or retained in a compressed state to achieve the collapsed configuration. In embodiments, the frame can self-transition from a collapsed configuration to an expanded configuration. A sleeve or other retaining member may be used to retain the frame in the collapsed configuration. The retaining member may be withdrawn from about the frame when the frame is properly positioned to allow the frame to expand and engage tissue of the patient. In embodiments, the frame may be actively expanded from a collapsed configuration to an expanded configuration. For example, the frame may be expanded by a spring or other biasing mechanism, by a balloon, or the like.

In embodiments, the frame, or one or more portions thereof, is formed from shape memory material that is self-expandable from a collapsed configuration to an expandable configuration by the application of heat, energy, or the like, or by the removal of external forces (e.g., compressive forces applied by a retaining member). Any suitable shape memory material may be employed. One example of a suitable shape memory material is a nickel-titanium alloy, such as NITINOL.

Preferably, the frame can be collapsed and expanded multiple times without damaging the structure of the frame.

A frame of a ventricular assist device may be delivered to the patient in any suitable manner. In embodiments, the frame is delivered via a catheter; e.g., a transcatheter. Examples of suitable delivery systems for embodiments of frames disclosed herein (and suitable frames) are disclosed in US 2011/0098805, entitled TRANSCATHETER VALVE DELIVERY SYSTEMS AND METHODS, which published patent application is hereby incorporated herein by reference in its entirety to the extent that it does not conflict with the present disclosure.

One or more pump assembly component may be coupled to the expanded frame that is implanted in the patient. The one or more pump assembly components, in various embodiments, can be delivered to the implanted frame for attachment to the frame via a catheter; e.g., a transcatheter.

The pump components may be coupled to the frame or to each other via any suitable features. In embodiments, the components are attached to the frame or each other via one way clips or retention features.

In embodiments, one or more of the pump assembly components are minipumps. Minipumps are self-contained pumps that typically pump low volumes of fluid, such as about 1 liter/minute. Accordingly, more than one minipump may be employed and coupled to the frame. For example, if a micropump pumps about 1 L/min, from about 5 to about 8 pumps may be desired to simulate cardiac output.

In embodiments, the pump assemblies are impeller-type pumps. In embodiments, the impeller includes a shaft and impellers that are coupled to the frame prior to implanting the frame. A housing or housing components may then be coupled to the shaft (and thus operably coupled to the frame) after the frame and shaft are implanted.

With the above understanding in mind, some specific embodiments of VADs, components of VADs, delivery systems and methods are described below.

Figure 1B:
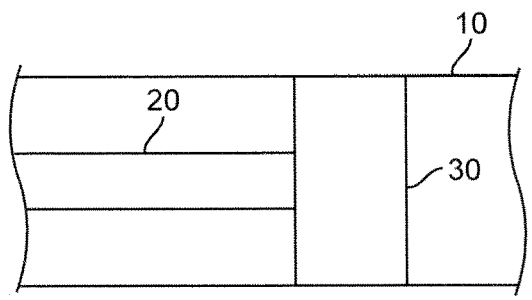
Figure 1C:
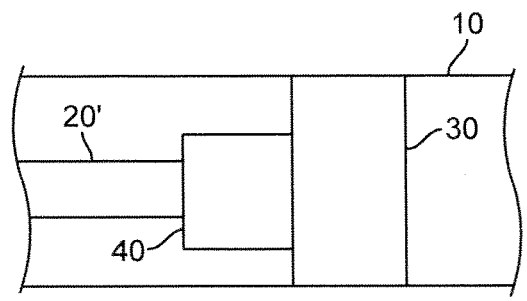
Figure 1D:
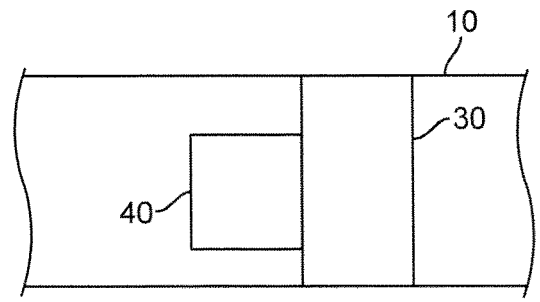

Referring now to FIGS. 1A-D schematic drawings illustrating an overview of a procedure for implanting a VAD as shown. A transcatheter 20 is employed to navigate a frame 30 through a patient's vasculature to a desired location within a blood vessel 10 (FIG. 1A). The frame 30 is then expanded or allowed to expand to engage an inner wall of the vessel 10 (FIG. 1B). The frame 10 may be expanded or allowed to expand in any suitable manner; e.g., as described above. For example, a sheath (not shown) may be withdrawn from around the frame (e.g, as described in US 2011/0098805, a balloon (not shown) may be used to expand the frame, or the like. A catheter 20' may then be employed to navigate a pump 40 or pump component through a patient's vasculature to the implanted and expanded frame 30 such that the pump 40 or component may be coupled to the frame (FIG. 1C). The catheter 20' used for delivering the pump 40 or component may the same or different from the catheter 20 used to deliver the frame 30. The catheter 20' may be withdrawn, leaving the pump 40 and frame (collectively, the VAD), implanted in the vessel 10.

Figure 2A:
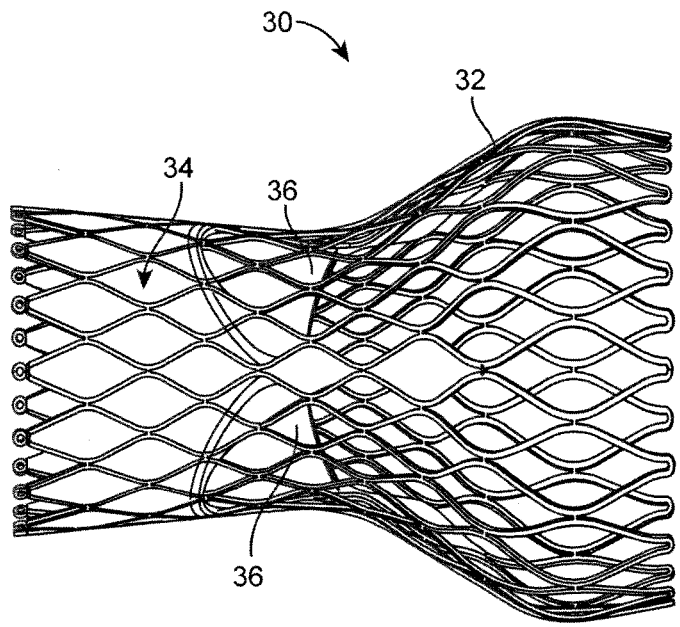
FIGS. 2A-B are schematic side views of a heart valve, which includes an embodiment of a frame, in an expanded (2A) and a collapsed (2B) configuration.
Figure 2B:
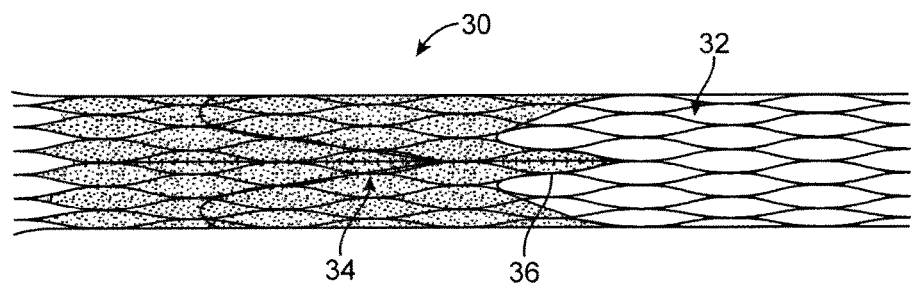

Referring now to FIGS. 2A-B, an example of a frame 30 that is a heart valve that may be employed for purposes of coupling a pump assembly is shown. In FIG. 2A, the frame 30 is in an expanded configuration. In FIG. 2B, the frame 30 is in a collapsed configuration. In the depicted embodiment, the frame is a heart valve and includes a stent frame 32 and a valve structure 34 that provides two or more leaflets 36. In embodiments, the frame is not part of a heart valve and thus does not include a valve structure.

Referring now to FIGS. 3A-B, a sectional view of a frame 30, in this case an entire heart valve including leaflets 36, is shown implanted in vessel 10, in this case an aorta. The frame 30 includes an extension 39 to which a pump 40 or a pump component may couple. In FIG. 3B, a bottom-up view of the frame extension 39 is shown, illustrating a scaffold 38 having openings configured to receive pumps 40 or pump components. In FIG. 3C, a sectional view of a pump 40 and a portion of the scaffold are shown, illustrating the pump 40 fitted into a seat 37 or seal of the scaffold. The scaffold 38 can be part of the frame 30 design or a separate section that is implanted after the frame is implanted and attached to the main frame design. The scaffold may be crimped down to fit into a delivery catheter. Like the frame, the scaffold is collapsible and expandable. In embodiments, the scaffold can be the frame.

Figure 4A:
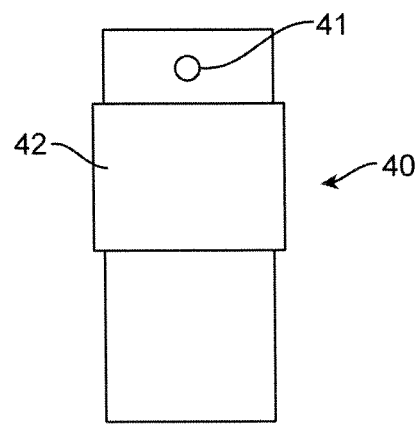
FIGS. 4A-C are schematic diagrams of embodiments of a ventricular assist device or components thereof.
Figure 4B:
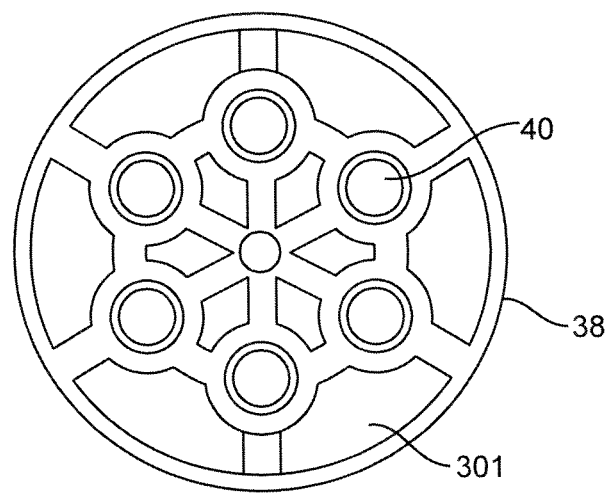
Figure 4C:
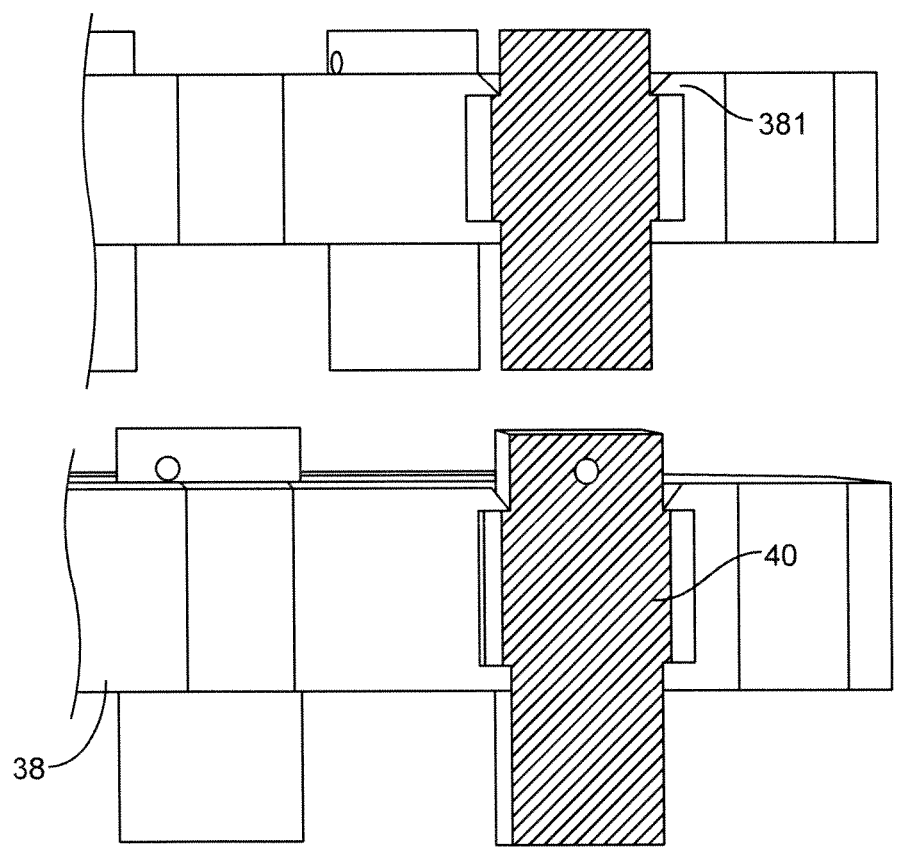
Figure 5A:
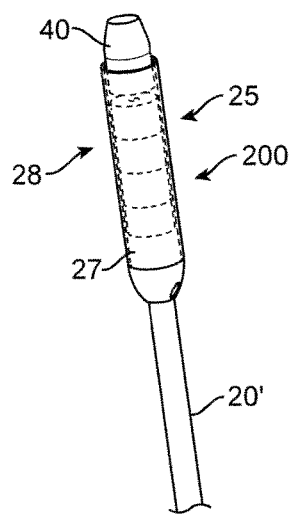
FIGS. 5A-D are schematic diagrams of embodiments of a ventricular assist device, a delivery system, or components thereof.
Figure 5B:
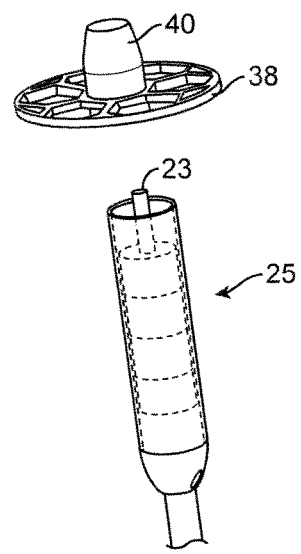
Figure 5C:
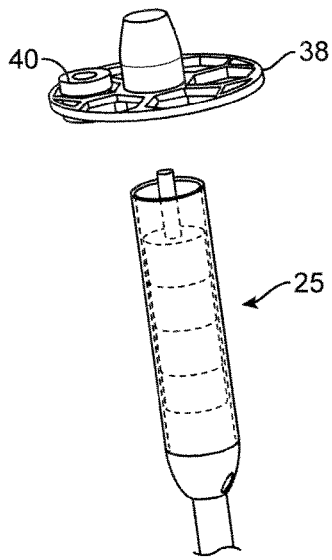
Figure 5D:
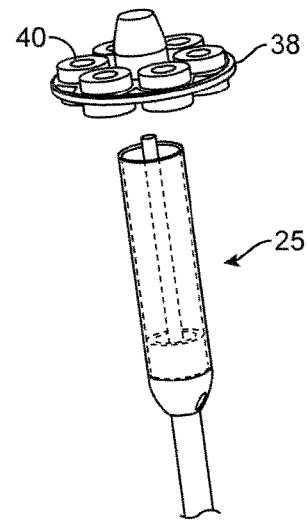

Referring now to FIGS. 4A-4C, embodiments of pumps 40 or pump components securably insertable into an embodiment of a scaffold 38 are shown. As depicted in FIG. 4A, a pump 40 or component may include a delivery system attachment element 41, such as a indent, detent, clip, or the like. The delivery system (not shown) can include a complementary attachment feature. The pump 40 or component depicted in FIG. 4A also includes a sleeve 42 or other seal disposed about a housing of the pump 40 or pump component. Openings in a scaffold 38 are configured to receive pumps 40 or components (see FIG. 4B). As depicted in FIG. 4B, the scaffold may include a polyester skirt 301 or skirt of other suitable material such that fluid flows only or primarily through the pumps.

Referring now to FIG. 4C specifically, the scaffold includes a one-way capture element 381 and a cavity configured to receive the sleeve or seal of pump 40. The capture element 381 cooperates with the sleeve of the pump in the depicted embodiment to allow passage of the sleeve into the cavity of the scaffold and to retain the sleeve in the cavity. The outer diameter of the sleeve is greater than the diameter of the opening created by the capture element 381. The capture element 381 is tapered on one surface to facilitate passage of the sleeve into the cavity. The opposing surface of the capture element 381 is not tapered and thus resists withdrawal of the pump (via interaction with a shoulder of the sleeve) once inserted. The diameter of the opening on the surface of the scaffold opposing the capture element 381 is smaller than the outer diameter of the sleeve of the pump 40 in the depicted embodiment to prevent further insertion of the pump (beyond a point where the sleeve engages the surface defining the opening opposing the capture element). Preferably, the pump is sealingly engaged by the scaffold when seated in the scaffold.

It will be understood that the mechanism for coupling a pump or pump component to a frame depicted in, and described with regard to, FIG. 4C is only one example of a coupling mechanism and that any other suitable coupling mechanism such as a clap, other snap fit mechanism, or the like may be used and are contemplated herein.

Referring now to FIGS. 5A-D, an embodiment of a pump assembly delivery system 200 for delivering and coupling embodiments of pumps 40 or pump components to an embodiment of a scaffold 38 of a frame is depicted. The delivery system includes a catheter body 20' and a distal pump retention and delivery element 25. The pump retention and delivery element includes an open-ended housing 28 configured to receive and retain pumps 40 or pump components. The pump retention and delivery element 25 may also include a shaft 23 about with the pumps 40 or pump components may be disposed. The pumps 40 or pump components have lumens or cavities configured to receive the shaft 23. The shaft 23 facilitates stacking of pumps 40 or pump components within the housing 28. The pump retention and delivery element 25 further includes a pushing element 27 to push pumps 40 or pump components from housing 28 and into coupling arrangement with scaffold 38 of frame. The scaffold 38 is collapsible and expandable; e.g. as described above with regard to other scaffold or frame embodiments. In the embodiment depicted in FIGS. 5A-D, the scaffold 38 includes hexagonal openings for receiving hexagonally shaped pumps 40 or pump components. The first pump 40 or pump component to be deployed may include a tip feature as depicted. The tip feature may serve as an atraumatic tip to ease insertion of the delivery system. The pumps 40 or pump components may be deployed one at a time into a respective opening formed in the scaffold 38. The pumps 40 or pump components may be retained relative to the scaffold 38 via any suitable retention mechanism, such as claps, one-way snap fit, or the like.

Referring now to FIGS. 6A-C, an embodiment of a pump assembly delivery system 200 for delivering and coupling embodiments of pumps 40 or pump components to an embodiment of a scaffold 38 of a frame is depicted. The delivery system 200 depicted in FIGS. 6A-C includes a catheter body 20', a pump retention and delivery element 25 that has a housing 28, shaft 23 and pushing element 27. The delivery system 200 depicted in FIGS. 6A-C may be operated in the same manner as, or similar manner to, the delivery system depicted in FIGS. 5A-D. As depicted in FIGS. 6A-C, the pumps 40 or pump components may be deployed around a circumference of a scaffold 28 (which may be a portion of the frame) and then in the center. The pumps 40 or components may couple to the scaffold 38 or each other through side features on the pumps 40 or components, one-way clips, or the like. The pumps 40 or components are hexagonally shaped in the depicted embodiment and may be coupled to form a honey-comb pattern as depicted.

Figure 7A:
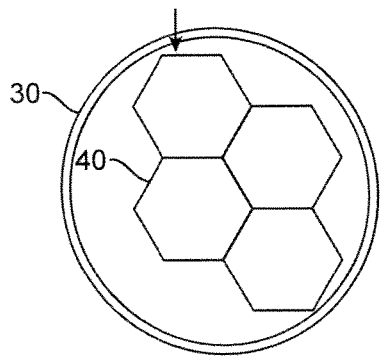
FIGS. 7A-B are schematic diagrams of embodiments of a ventricular assist device or components thereof.
Figure 7B:
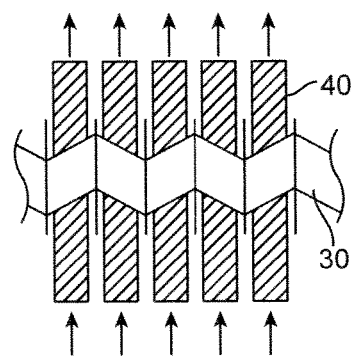

Referring now to FIGS. 7A-B, pumps 40 or pump components are shown operably coupled to a frame 30. FIG. 7A shows top view, and FIG. 7B shows a side view. The arrows in FIG. 7B show the direction of flow through the pumps 40. In the depicted embodiment, the pumps 40 or pump components are hexagonal and may be coupled to form a honey-comb pattern. The pumps 40 or pump components may be coupled via snap fit, or any other suitable mechanism, to the frame 30.

Figure 8:
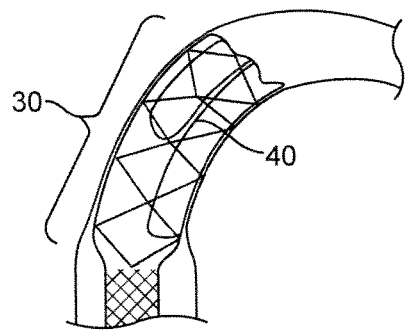
FIG. 8 is schematic diagrams of embodiments of a ventricular assist device or components thereof.

Referring now to FIG. 8, pumps 40 or pump components are shown operably coupled to various locations of a frame 30. The length of the frame 30 may be configured to accommodate any suitable number of pumps 40 or pump components.

Referring now to FIGS. 9A-9D, embodiments of pumps 40 or pump components, frame 30 and delivery system 200 are shown. In FIG. 9A, the frame 30 is shown implanted in a vessel 10 of a patient, in this case the aorta. Pumps 40 or pump components are operably coupled to the frame. In FIG. 9B, a delivery system 200 is depicted. The delivery system 200 may be used in a manner similar to the delivery systems depicted in, and described with regard to, FIGS. 5-6. Like the delivery systems depicted in FIGS. 5-6, the delivery system 200 depicted in FIG. 9B includes a catheter body 20', a pump retention and delivery element 25 that has a housing 28 and a shaft 23; and may have a pushing element 27. The pump retention and delivery element 25 also includes a distal expandable and collapsible member 21. Member 21 can be expanded while the delivery system is navigated through the patient and can be collapsed to deliver the pumps 40 or pump components to couple the pumps or components to a frame or each other. The delivery system 200 may be configured in a manner similar to a clip on a gum, but in series. Of course, other suitable configurations suitable for deploying pumps or pump components may be used. As shown in FIG. 9C, the pumps 40 or pump components may be hexagonal and may be deployed in a honey comb shaped arrangement. As shown in FIG. 9D, the pump 40 or pump component may include a housing 41 and retention features 42 for coupling the pump 40 or component to a frame or to another pump or pump component. In the embodiment depicted in FIG. 9D, the retention features 42 extend from a side of the housing 41. Any suitable retention feature 42 may be employed, such as the hook and eye features depicted in FIG. 9D.

Figure 10A:
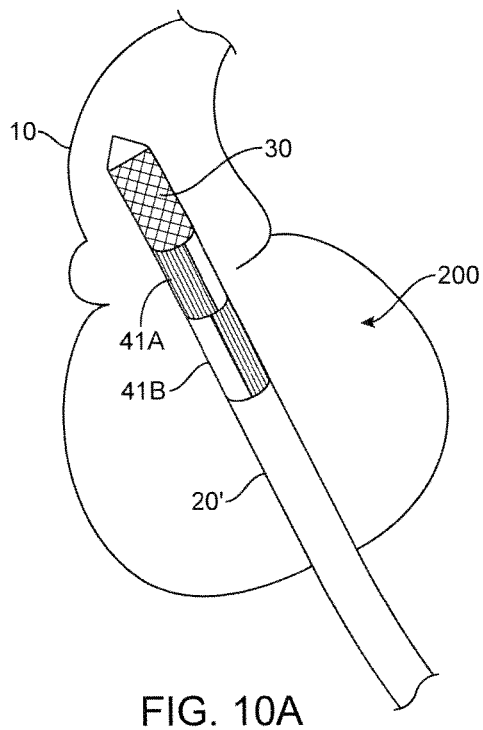
FIGS. 10A-E are schematic diagrams of embodiments of a ventricular assist device, a delivery system, or components thereof.
Figure 10C:
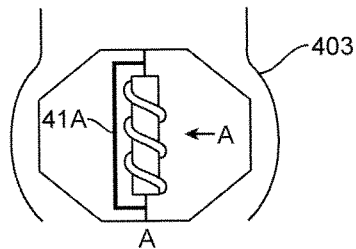
Figure 10D:
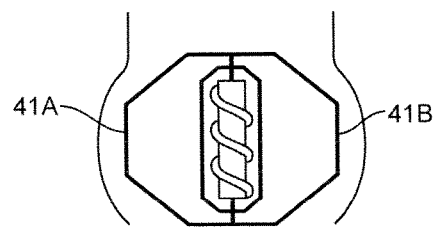
Figure 10B:
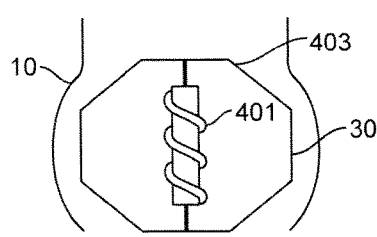
Figure 10E:
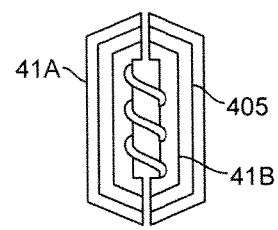

Referring now to FIGS. 10A-E, embodiments of a pump or pump components, frame 30 and delivery system 200 are shown. The frame 30 and pump are delivered in three stages in the depicted embodiment. The delivery system 200 depicted in FIG. 10A is configured to deliver frame 30, first part of pump housing 41A and second part of pump housing 41B. In FIG. 10B, the frame is depicted in its expanded configuration engaging an aorta 10. A shaft 403 and impeller 401, which are pump components, are coupled to the frame 30 prior to deployment of the frame (i.e., outside the patient or during manufacture). The first housing part 41A is coupled to the shaft 403; e.g, clipped to the shaft (see FIG. 10C), then the second housing part 41B of the pump assembly is coupled and sealingly engaged with the first housing part 41B (see FIG. 10C). An o-ring 450, flange, or other seal may aid in sealing the two housing parts 41A, 41B; e.g., as depicted in FIG. 10E. One or more electrical components for powering or controlling the shaft/impeller may be included with the first 41A or second 41B housing part.

The pumps, pump components, frames and delivery systems depicted with regard to any one figure or embodiment may be used or modified for use with any other suitable embodiment depicted or described herein.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

Thus, embodiments of MODULAR VENTRICULAR ASSIST DEVICE are disclosed. One skilled in the art will appreciate that the leads, devices such as signal generators, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. A method comprising:
   implanting a frame in a vessel;
   attaching a scaffold having an opening to the implanted frame;
   advancing a pump component through the vessel from a location away from the implanted frame into the scaffold opening; and
   operably coupling the pump component to the scaffold.

2. The method of claim 1, wherein the pump component comprises a micropump.

3. The method of claim 1, wherein implanting the frame in the vessel comprises engaging the vessel with the frame.

4. The method of claim 1, wherein the pump component is configured to pump fluid through the frame along a longitudinal axis of the frame.

5. The method of claim 1, further comprising advancing the frame through the vessel prior to implanting the frame.

6. The method of claim 5, wherein advancing the frame through the vessel comprises advancing the frame a distance of greater than 50 cm.

7. The method of claim 1, further comprising advancing the scaffold through the vessel prior to attaching the scaffold to the frame.

8. The method of claim 7, wherein advancing the scaffold through the vessel comprises advancing the scaffold a distance of greater than 50 cm.

9. The method of claim 1, wherein advancing the pump component through the vessel comprises advancing the pump component a distance of greater than 50 cm.

10. The method of claim 1, wherein the frame has an expanded configuration and a collapsed configuration.

11. The method of claim 1, wherein the scaffold has an expanded configuration and a collapsed configuration.

12. The method of claim 1, further comprising a heart valve attached to the frame.

13. The method of claim 1, wherein the vessel is an aorta and the frame is configured to securely engage an inner wall of the aorta when implanted.

14. The method of claim 1, wherein the frame is configured to be delivered through the vessel via an intravascular catheter.

15. The method of claim 1, wherein the scaffold is configured to be delivered through the vessel via an intravascular catheter.

16. The method of claim 1, wherein the pump component is configured to be delivered through the vessel via an intravascular catheter.

* * * * *